(12) United States Patent
Scates et al.

(10) Patent No.: US 8,017,802 B2
(45) Date of Patent: Sep. 13, 2011

(54) CONTROL OF IMPURITIES IN REACTION PRODUCT OF RHODIUM-CATALYZED METHANOL CARBONYLATION

(75) Inventors: Mark O. Scates, Houston, TX (US); G. Paull Torrence, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 809 days.

(21) Appl. No.: 11/804,882

(22) Filed: May 21, 2007

(65) Prior Publication Data

US 2008/0293966 A1 Nov. 27, 2008

(51) Int. Cl.
*C07C 53/08* (2006.01)
*C07C 51/42* (2006.01)
*C07C 53/00* (2006.01)

(52) U.S. Cl. .......... 562/607; 562/608; 562/609
(58) Field of Classification Search .............. None
See application file for complete search history.

(56) References Cited

U.S. PATENT DOCUMENTS

2002/0151746 A1* 10/2002 Scates et al. .................. 562/519

\* cited by examiner

*Primary Examiner* — Paul A Zucker

(57) ABSTRACT

The present invention relates to carbonylation of methanol, methyl acetate, dimethyl ether or mixtures thereof to produce glacial acetic acid, and more specifically to the manufacture of glacial acetic acid by the reaction of methanol, methyl acetate, dimethyl ether or mixtures thereof with carbon monoxide wherein the product glacial acetic acid contains low impurities.

14 Claims, 4 Drawing Sheets

Figure 1:
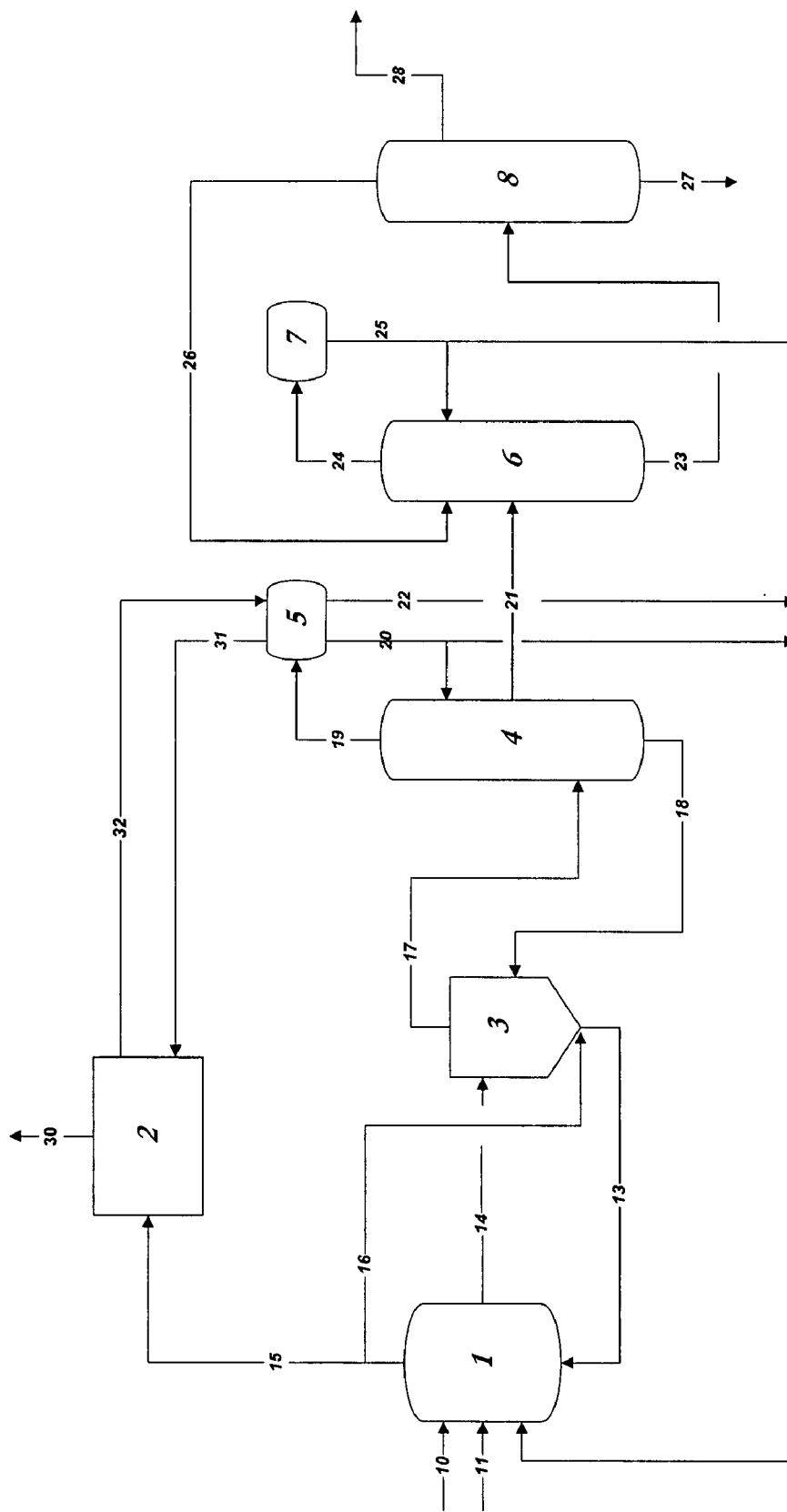

CONTROL OF IMPURITIES IN REACTION PRODUCT OF RHODIUM-CATALYZED METHANOL CARBONYLATION

I. FIELD OF INVENTION

The present invention relates to a method for carbonylation of methanol, methyl acetate, dimethyl ether or mixtures thereof to produce glacial acetic acid, and more specifically to the manufacture of glacial acetic acid by the reaction of methanol, methyl acetate, dimethyl ether or mixtures thereof with carbon monoxide wherein the product glacial acetic acid contains low impurities.

II. BACKGROUND OF THE INVENTION

A. Methanol Carbonylation to Produce Acetic Acid

For the production of acetic acid, there are three major commercialized processes, the carbonylation process, acetaldehyde oxidation process, and liquid phase oxidation process, wherein the carbonylation process accounts for about 70% of the world manufacturing capacity. Among currently employed processes for synthesizing acetic acid, one of the most useful commercially is the catalyzed carbonylation of methanol as taught in U.S. Pat. No. 3,769,329 issued to Paulik et al. on Oct. 30, 1973. The carbonylation catalyst comprises rhodium, either disolved or otherwise dispersed in a liquid reaction medium or else supported on an inert solid, along with a halogen-containing catalyst promoter as exemplified by methyl iodide. Generally, the reaction is conducted with the catalyst being dissolved in a liquid reaction medium, through which carbon monoxide gas is continuously bubbled. Paulik et al. disclose that water may be added to the reaction mixture to exert a beneficial effect upon the reaction rate, and water concentrations between about 14-15 wt % are typically used. This is the so-called "high water" carbonylation process.

An important aspect of the teachings of Paulik et al. is that water should also be present in the reaction mixture in order to attain a satisfactorily high reaction rate. The patentees have a large number of reaction systems as examples including a large number of applicable liquid reaction media. The general thrust of their teachings is, however, that a substantial quantity of water helps in attaining an adequately high reaction rate. The patentees also teach that reducing the water content leads to the production of ester as opposed to carboxylic acid. Considering specifically the carbonylation of methanol to acetic acid in a solvent comprising predominantly acetic acid and using the promoted catalyst taught by Paulik et al., it is taught in European Patent Application No. 0 055 618 that typically about 14-15 wt % water is present in the reaction medium of a typical acetic acid plant using this technology. It will be seen that in recovering acetic acid in anhydrous or nearly anhydrous form from such a reaction solvent, and separating the acetic acid from this appreciable quantity of water, involves a substantial expenditure of energy in distillation and/or additional processing steps such as solvent extraction, as well as enlarging some of the process equipment compared with that used in handling drier materials. Also Hjortkjaer and Jensen [Ind. Eng. Chem., Prod. Res. Dev. 16, 281-285 (1977)] have shown that increasing the water from 0 to 14 wt % water increases the reaction rate of methanol carbonylation. Above 14 wt % water, the reaction rate is unchanged.

In addition, as will be further explained hereinbelow, the catalyst tends to precipitate out of the reaction medium as employed in the process of Paulik et al., especially during the course of distillation operations to separate the product from the catalyst solution when the carbon monoxide content of the catalyst system is reduced (EP0055618). It is known that this tendency increases as the water content of the reaction medium is decreased. Thus, although it might appear obvious to try to operate the process of Paulik et al. at minimal water concentration in order to reduce the cost of handling a reaction product containing a substantial amount of water while still retaining enough water for an adequate reaction rate, the requirement for appreciable water in order to maintain catalyst activity and stability works against this end.

Other reaction systems are known in the art in which an alcohol such as methanol or an ether such as dimethyl ether or an ester such as methyl acetate can be carbonylated to an acid or ester derivative using special solvents such as aryl esters of the acid under substantially anhydrous reaction conditions. The product acid itself can be a component of the solvent system. Such a process is disclosed in U.S. Pat. No. 4,212,989 issued on Jul. 15, 1975 to Isshiki et al., with the catalytic metal being a member of the group consisting of rhodium, palladium, iridium, platinum, ruthenium, osmium, cobalt, iron, and nickel. A somewhat related patent is U.S. Pat. No. 4,336,399 issued to the same patentees, wherein a nickel-based catalyst system is employed. Considering U.S. Pat. No. 4,212,989 in particular, the relevance to the present invention is that the catalyst comprises both the catalytic metal, as exemplified by rhodium, along with what the patentees characterize as a promoter, such as the organic iodides employed by Paulik et al. as well as what the patentees characterize as an organic accelerating agent. The accelerating agents include a wide range of organic compounds of trivalent nitrogen, phosphorus, arsenic, and antimony. Sufficient accelerator is used to form a stoichiometric coordination compound with the catalytic metal. Where the solvent consists solely of acetic acid, or acetic acid mixed with the feedstock methanol, only the catalyst promoter is employed (without the accelerating agent), and complete yield data are not set forth. It is stated, however, that in this instance "large quantities" of water and hydrogen iodide were found in the product, which was contrary to the intent of the patentees.

European Published Patent Application No. 0 055 618 belonging to Monsanto Company discloses carbonylation of an alcohol using a catalyst comprising rhodium and an iodine or bromine component wherein precipitation of the catalyst during carbon monoxide-deficient conditions is alleviated by adding any of several named stabilizers. A substantial quantity of water, of the order of 14-15 wt %, was employed in the reaction medium. The stabilizers tested included simple iodide salts, but the more effective stabilizers appeared to be any of several types of specially selected organic compounds. There is no teaching that the concentrations of methyl acetate and iodide salts are significant parameters in affecting the rate of carbonylation of methanol to produce acetic acid especially at low water concentrations. When an iodide salt is used as the stabilizer, the amount used is relatively small and the indication is that the primary criterion in selecting the concentration of iodide salt to be employed is the ratio of iodide to rhodium. That is, the patentees teach that it is generally preferred to have an excess of iodine over the amount of iodine, which is present as a ligand with the rhodium component of the catalyst. Generally speaking, the teaching of the patentees appears to be that iodide which is added as, for example, an iodide salt, functions simply as a precursor component of the catalyst system. Where the patentees add hydrogen iodide, they regard it as a precursor of the promoter methyl iodide. There is no clear teaching that simple iodide ions as such are of any significance or that it is desirable to have them present in substantial excess to increase the rate of the reaction. As a matter of fact, Eby and Singleton [Applied Industrial Catalysis, Vol. 1, 275-296(1983)] from Monsanto state that iodide salts of alkali metals are inactive as co-catalyst in the rhodium-catalyzed carbonylation of methanol.

Carbonylation of esters, such as methyl acetate, or ethers, such as dimethyl ether, to form a carboxylic acid anhydride such as acetic anhydride is disclosed in U.S. Pat. No. 4,115,444 to Rizkalla and in European Patent Application No. 0,008,396 by Erpenbach et al. and assigned to Hoechst. In both cases the catalyst system comprises rhodium, an iodide, and a trivalent nitrogen or phosphorus compound. Acetic acid can be a component of the reaction solvent system, but it is not the reaction product. Minor amounts of water are indicated to be acceptable to the extent that water is found in the commercially available forms of the reactants. However, essentially dry conditions are to be maintained in these reaction systems. U.S. Pat. No. 4,374,070 issued to Larkins et al. teaches the preparation of acetic anhydride in a reaction medium, which is, of course, anhydrous by carbonylating methyl acetate in the presence of rhodium, lithium, and an iodide compound. The lithium can be added as lithium iodide. Aside from the fact that the reaction is a different one from that with which the present invention is concerned, there is no teaching that it is important per se that the lithium be present in any particular form such as the iodide. There is no teaching that iodide ions as such are in significant amounts.

U.S. Pat. No. 5,001,259, U.S. Pat. No. 5,026,908 and U.S. Pat. No. 5,144,068 disclose a rhodium-catalyzed low water method for the production of acetic acid. Methanol is reacted with carbon monoxide in a liquid reaction medium containing a rhodium catalyst stabilized with an iodide salt, especially lithium iodide, along with alkyl iodide such as methyl iodide and alkyl acetate such as methyl acetate in specified proportions. This reaction system not only provides an acid product of unusually low water content (lower than 14 weight %) at unexpectedly favorable reaction rates but also, whether the water content is low or, as in the case of prior-art acetic acid technology, relatively high, it is characterized by unexpectedly high catalyst stability, i.e., it is resistant to catalyst precipitation out of the reaction medium. Employing a low water content simplifies downstream processing of the desired carboxylic acid to its glacial form.

Various means for removing iodide impurities from acetic acid are well know in the art. It was discovered by Hilton that macroreticular (macroporous) strong acid cation exchange resins with at least one percent of their active sites converted to the silver or mercury form exhibited remarkable removal efficiency for iodide contaminants in acetic acid or other organic media. The amount of silver or mercury associated with the resin may be from as low as about one percent of the active sites to as high as 100 percent. Preferably about 25 percent to about 75 percent of the active sites were converted to the silver or mercury form and most preferably about 50 percent. The subject process is disclosed in U.S. Pat. No. 4,615,806 for removing various iodides from acetic acid. In particular there is shown in the examples removal of methyl iodide, HI, $I_2$ and hexyl iodide.

Various embodiments of the basic invention disclosed in U.S. Pat. No. 4,615,806 have subsequently appeared in the literature. There is shown in U.S. Pat. No. 5,139,981 to Kurland a method for removing iodides from liquid carboxylic acid contaminated with a halide impurity by contacting the liquid halide contaminant acid with a silver (I) exchanged macroreticular (macroporous) strong acid cation exchange resin. The halide reacts with the resin bound silver and is removed from the carboxylic acid stream. The invention in the '981 patent more particularly relates to an improved method for producing the silver exchanged macroreticular (macroporous) strong acid cation exchange resins suitable for use in iodide removal from acetic acid.

U.S. Pat. No. 5,227,524 to Jones discloses a process for removing iodides using a particular silver-exchanged macroreticular (macroporous) strong acid cation exchange resin. The resin has from about 4 to about 12 percent cross-linking, a surface area in the proton exchanged form of less than 10 $m^2/g$ after drying from the water wet state and a surface area of greater than 10 $m^2/g$ after drying from a wet state in which the water has been replaced by methanol. The resin has at least one percent of its active sites converted to the silver form and preferably from about 30 to about 70 percent of its active sites converted to the silver form.

U.S. Pat. No. 5,801,279 to Miura et al. discloses a method of operating a silver exchanged macroreticular (macroporous) strong acid cation exchange resin bed for removing iodides from a Monsanto type acetic acid stream. The operating method involves operating the bed silver-exchanged resin while elevating the temperatures in stages and contacting the acetic acid and/or acetic anhydride containing the iodide compounds with the resin. Exemplified in the patent is the removal of hexyl iodide from acetic acid at temperatures of from about 25° C. to about 45° C.

So also, other ion exchange resins have been used to remove iodide impurities from acetic acid and/or acetic anhydride. There is disclosed in U.S. Pat. No. 5,220,058 to Fish et al. the use of ion exchange resins having metal exchanged thiol functional groups for removing iodide impurities from acetic acid and/or acetic anhydride. Typically, the thiol functionality of the ion exchange resin has been exchanged with silver, palladium, or mercury.

There is further disclosed in European Publication No. 0 685 445 A1 a process for removing iodide compounds from acetic acid. The process involves contacting an iodide containing acetic acid stream with a polyvinylpyridine at elevated temperatures to remove the iodides. Typically, the acetic acid was fed to the resin bed according to the '445 publication at a temperature of about 100° C.

With ever increasing cost pressures and higher energy prices, there has been ever increasing motivation to simplify chemical manufacturing operations and particularly to reduce the number of manufacturing steps. In this regard, it is noted that in U.S. Pat. No. 5,416,237 to Aubigne et al. there is disclosed a single zone distillation process for making acetic acid. Such process modifications, while desirable in terms of energy costs, tend to place increasing demands on the purification train. In particular, fewer recycles tend to introduce (or fail to remove) a higher level of iodides into the product stream and particularly more iodides of a higher molecular weight. For example, octyl iodide, decyl iodide and dodecyl iodides may all be present in the product stream as well as hexadecyl iodide; all of which are difficult to remove by conventional techniques.

The prior art resin beds operated as described above do not efficiently and quantitatively remove impurities from acetic acid or acetic acid streams as required by certain end consumers, particularly the manufacture of vinyl acetate monomer (VAM). Accordingly, there is still a need to reduce the amounts of the impurities to a desired level in an acetic acid product stream.

B. Formation of Impurities in Methanol Carbonylation

It has been found that during the production of acetic acid by the carbonylation of methanol or methyl acetate in the presence of a finite amount of water, carbonyl impurities such as acetaldehyde, acetone, methyl ethyl ketone, butyraldehyde, crotonaldehyde, 2-ethyl crotonaldehyde, and 2-ethyl butyraldehyde and the like, are present and may further react to form aldol condensation products and/or react with iodide catalyst promoters to form multi-carbon alkyl iodides, i.e., ethyl iodide, butyl iodide, hexyl iodide and the like. While the presence of hydrogen in the carbonylation reaction does in fact increase the carbonylation rate, the rate of formation of undesirable by-products, such as crotonaldehyde, 2-ethyl crotonaldehyde, butyl acetate, and hexyl iodide, also increases.

In rhodium-catalyzed methanol carbonylation, the formation of formic acid impurities in the product acetic acid occurs. It has been discovered that the formic acid impurity in methanol carbonylation acetic acid product is caused by the reaction of carbon monoxide and water in the reaction medium:

$$CO + H_2O \rightarrow HCOOH$$

It has further been discovered that, under the known conditions of Rh catalyzed methanol carbonylation, the formic acid concentration in the product acetic acid is a direct function of the standing water concentration that is maintained in the carbonylation reaction medium. No other factors have been found to influence this relationship.

C. Disadvantages of Impurities

Glacial acetic acid is a raw material for several key petrochemical intermediates and products including VAM, acetate esters, cellulose acetate, acetic anhydride, monochloroacetic acid (MCA), etc., as well as a key solvent in the production of purified terephthalic acid (PTA).

Consumers of glacial acetic acid generally prefer a high purity product with as few impurities as possible and the lowest concentration on any contained impurities. The formic acid contained in product acetic acid is one such impurity and has numerous disadvantages making it an objectionable impurity for many acetic acid end uses. For example, high formic acid concentrations adversely affect the temperature and pressure control of p-xylene oxidation reactors in the terephthalic acid unit. Another example is where acetic acid is used as a feedstock for vinyl acetate (VAM) production. Formic acid impurity contained in the acetic acid generates undesirable carbon dioxide, which has to be removed from the VAM process. Traditional Monsanto technology of manufacturing acetic acid appears to produce about 175-220 ppm of formic acid in the finished acetic acid. Other methanol carbonylation acetic acid producers also produce high level of formic acid.

The iodide contamination can be of great concern to the consumers of the acetic acid as it may cause processing difficulties when the acetic acid is subjected to subsequent chemical conversion. A higher iodide environment could lead to increased corrosion problems and higher residual iodide in the final product. High iodide concentration in acetic acid could lead to catalyst poisoning problems in some downstream applications such as vinyl acetate monomer (VAM) manufacture.

III. SUMMARY OF THE INVENTION

One object of the invention is to provide a method of controlling impurities in a rhodium-catalyzed methanol carbonylation process for the manufacture of a glacial acetic acid product, comprising:
a) reacting methanol, methyl acetate, dimethyl ether or mixtures thereof with carbon monoxide in the presence of a rhodium catalyst in a reaction vessel;
b) maintaining in said reaction vessel a water concentration of 0.5 to 14 weight percent; such that the formic acid content in the resulting final glacial acetic acid product is controlled to an amount ranging from 15 ppm to 160 ppm; and
c) contacting the acetic acid obtained from step b) with a silver exchanged cationic ion exchange resin so that the total sulfur in the resulting final glacial acetic acid is in an amount less than 1 ppm.

According to the invention, the water concentration used in the method of the invention is preferably in an amount of 0.5 to 10 weight percent. More preferably, the water concentration is 0.5 to 8 weight percent. More preferably, the water concentration is 0.5 to 4 weight percent. According to the invention, the silver exchanged cation exchange resin is preferably a silver functionalized strong acid macroreticular (macroporous) cation exchange resin.

Another object of the invention is to provide a reaction product of a rhodium-catalyzed methanol carbonylation acetic acid manufacturing process characterized by a formic acid content in an amount less than 160 ppm and an amount of total sulfur in an amount less than 1 ppm. According to one embodiment of the invention, the reaction product of a rhodium-catalyzed methanol carbonylation process which maintains a reactor water concentration of 0.5 to 8 weight percent for the manufacture of glacial acetic acid, said reaction product characterized by a formic acid content of 15 ppm to 75 ppm. According another embodiment of the invention, the reaction product of a rhodium-catalyzed methanol carbonylation process which maintains a reactor water concentration of 0.5 to 4 weight percent for the manufacture of glacial acetic acid, said reaction product characterized by a formic acid content of 15 ppm to 35 ppm. According to another embodiment of the invention, during the treatment, the sulfur will be leached from the resin and leaves in the glacial acetic acid product at an amount less than 1 ppm. Preferably, the sulfur leached from the resin and left in the glacial acetic acid product is in an amount ranging from 20 to 800 ppb. More preferably, the sulfur leached from the resin and left in the glacial acetic acid product is in an amount ranging from 20 to 600 ppb. More preferably, the sulfur leached from the resin and left in the glacial acetic acid product is in an amount ranging from 20 to 400 ppb. More preferably, the sulfur leached from the resin and left in the glacial acetic acid product is in an amount ranging from 20 to 200 ppb. More preferably, the sulfur leached from the resin and left in the glacial acetic acid product is in an amount ranging from 20 to 100 ppb. More preferably, the sulfur leached from the resin and left in the glacial acetic acid product is in an amount ranging from 20 to 50 ppb. Most preferably, the sulfur leached from the resin and left in the glacial acetic acid product is in an amount ranging from 20 to 40 ppb.

As used herein, glacial acetic acid is concentrated, higher than 99.5% pure acetic acid. Glacial acetic acid is called "glacial" because its freezing point (16.7° C.) is only slightly below room temperature. In the (generally unheated) laboratories in which the pure material was first prepared, the acid was often found to have frozen into ice-like crystals. The term "glacial acetic acid" is now taken to refer to pure acetic acid (ethanoic acid) in any physical state.

IV. BRIEF DESCRIPTION OF THE DRAWINGS

Figure 2:
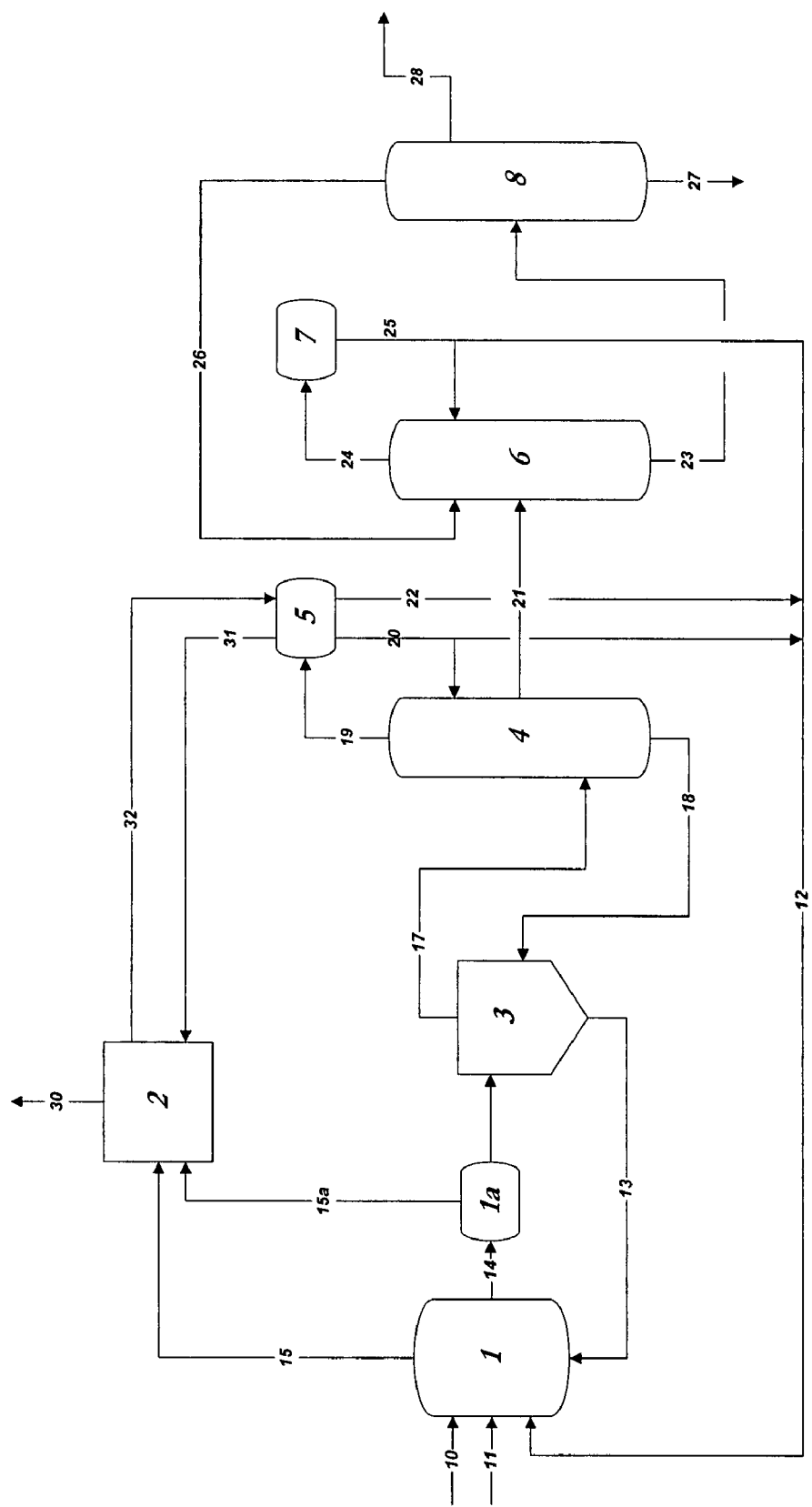
Figure 3:
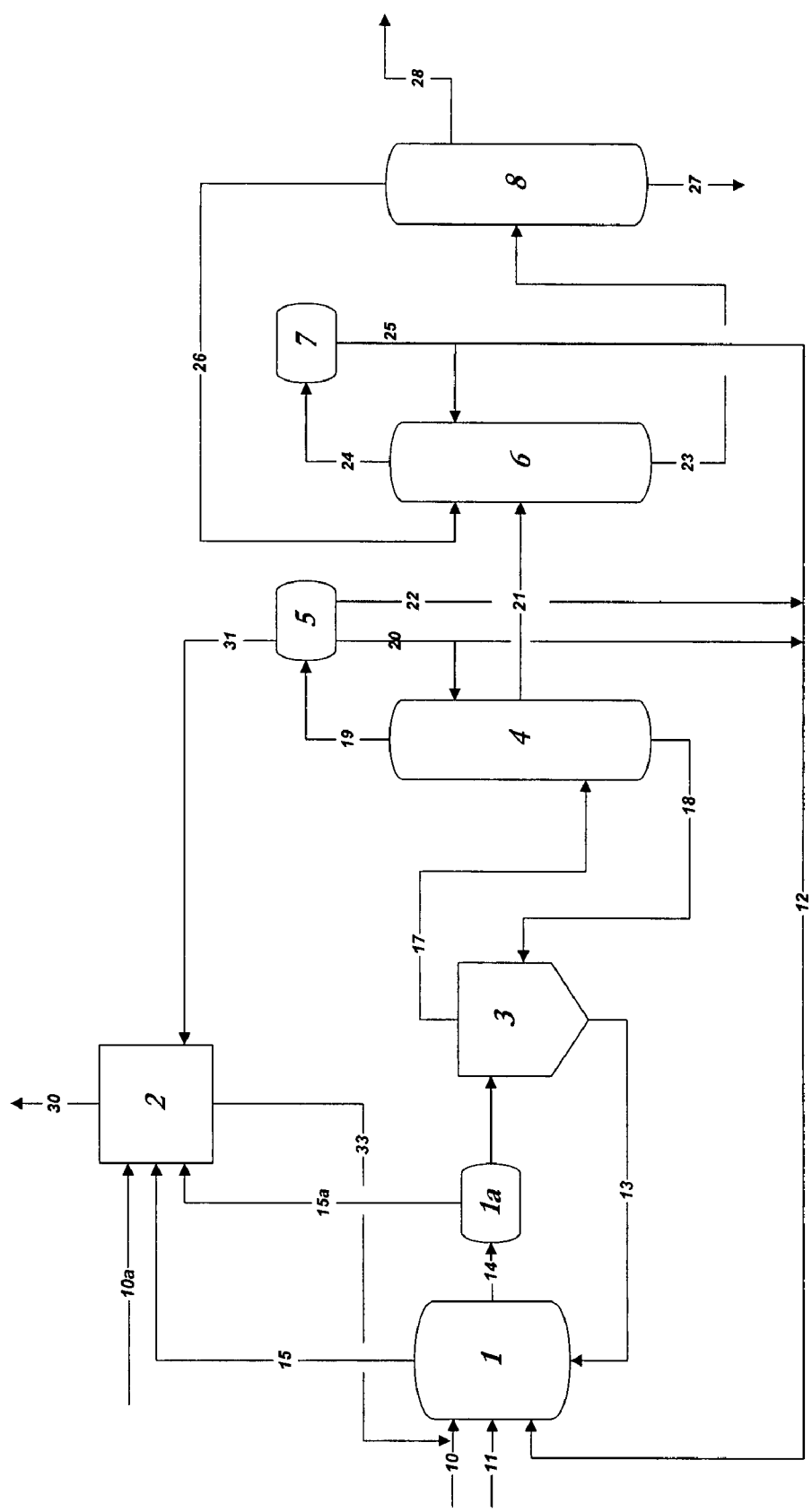

FIG. 1 is a process flow diagram illustrating a simplified typical generic rhodium-catalyzed methanol carbonylation process. Additional examples of other common flow variations for the methanol carbonylation process are illustrated in FIGS. 2 and 3. The variants in FIGS. 2 and 3 incorporate an optional converter between the reactor and flasher vessel and include vent gas scrubbing with either acetic acid or methanol. As illustrated in FIG. 1, a portion of the high pressure vent gas which contains CO can also be optionally used as a purge to the flasher base liquid to enhance Rh stability.

It is understood that FIGS. 1, 2 and 3 are merely typical examples of common flow patterns for a methanol carbonylation process. It is also understood that FIGS. 1, 2 and 3 are non-limiting to this invention and that there can be many alternative variations to this "typical" flow diagram within the scope of this invention.

Figure 4:
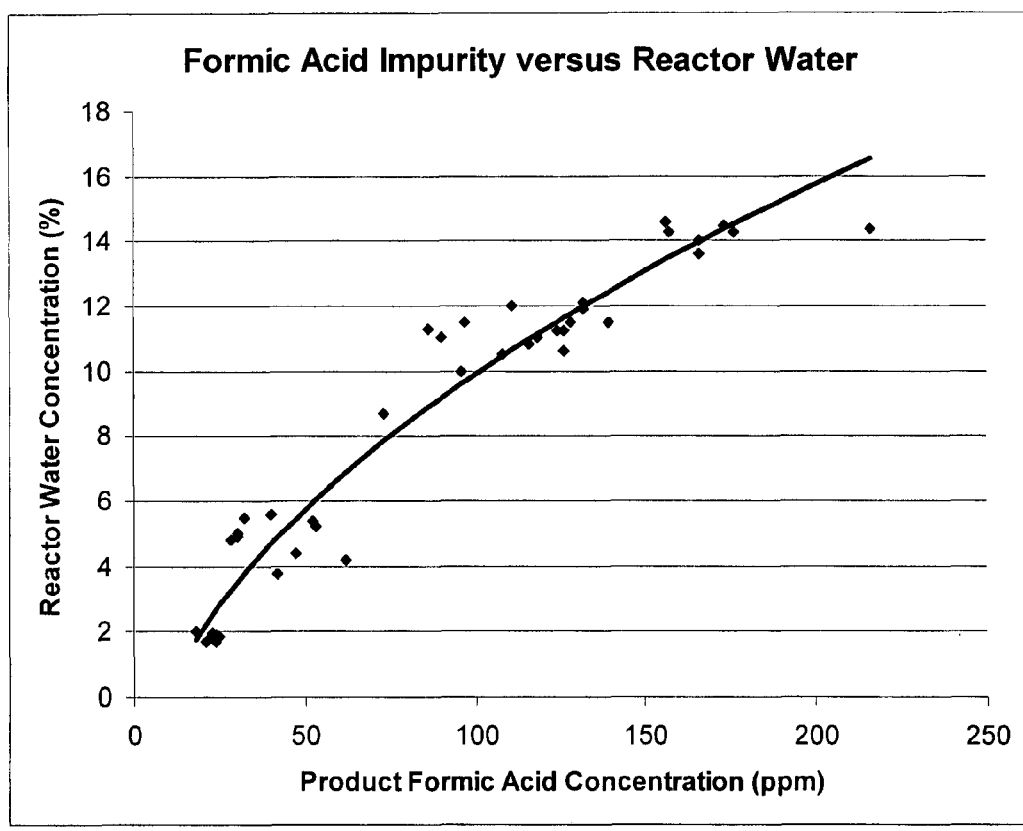

FIG. 4 is a graph of the experimental data illustrating formic acid impurity in glacial acetic acid product versus water concentration in the carbonylation reaction medium.

A list of reference symbols of the elements shown in the figures with corresponding element names is as follows:
1 reactor
1a converter 1a
2 gas scrubbing system
3 flasher
4 light ends column
5 light ends column decanter
6 drying columns
7 drying column reflux drum 7
8 heavy ends column
10 methanol
10a methanol
11 carbon monoxide
12 recycle stream
13 catalyst recycle
14 line
15 reactor vent line
15a line
17 line
18 line
19 light ends overhead stream
20 aqueous phase
21 line
22 organic phase
23 residue
24 line
25 line
26 line
27 heavy byproduct
28 glacial acetic acid product
30 line
31 purification system vent line
32 recycled light ends
33 line

V. DETAILED DESCRIPTION OF THE INVENTION

A. General Rhodium-Catalyzed Methanol Carbonylation Reaction to Make Acetic Acid To produce acetic acid by methanol carbonylation, methanol is reacted with carbon monoxide in the presence of a catalyst. The general formula is as follows:

$$CH_3OH + CO \rightarrow CH_3COOH$$

In the practice of the present invention, rhodium is used as the catalyst in methanol carbonylation process and renders the process highly selective. Methyl iodide is used as a promoter and an iodide salt is maintained in the reaction medium to enhance stability of the rhodium catalyst. Water is also maintained from a finite amount up to 14 weight % in the reaction medium. A reaction system which can be employed, within which the present improvement is used, will be further explained below, comprises:

(a) a liquid-phase or slurry type carbonylation reactor which optionally may include a so-called "converter" reactor, (b) a "flasher" vessel, and (c) a purification system consisting of distillation and vent scrubbing using two or more columns to separate volatile components comprising methyl iodide, methyl acetate, water and other light ends and generate a purified glacial acetic acid product.

B. General Process Flow

1. Reactor

Referring to FIG. 1, methanol and carbon monoxide are fed into a reaction vessel, i.e., a reactor 1. The carbonylation reactor is typically a stirred autoclave, bubble column reactor vessel or gas-liquid educed vessel within which the reacting liquid or slurry content is maintained automatically at a constant level. Carbon monoxide is fed via line 11 to the reactor. Into this reactor the fresh carbonylatable reactants (such as methanol, methyl acetate, dimethyl ether and/or mixtures thereof) are continuously introduced via a methanol feed 10; a recycle stream 12 including water, methyl iodide and methyl acetate from the overhead of the light ends column 4 and drying columns 6, the catalyst recycle 13 from the base of the flasher 3, and optionally a fresh water makeup (if needed) to maintain at least a finite concentration of water in the reaction medium are also continuously introduced. Continuous fresh water feed is needed to maintain a finite water concentration in the reaction medium when the feedstock is methyl acetate and/or dimethyl ether. When the feedstock is methanol, a continuous fresh water feed may or may not be needed depending upon the rate of water consumption via the known water gas shift reaction. Alternate distillation systems can be employed so long as they provide means for recovering a crude acetic acid and directly or indirectly recycling to the reactor catalyst solution components such as methyl iodide, water, methyl acetate and rhodium. Carbon monoxide is also continuously introduced into the carbonylation reactor. The carbon monoxide is thoroughly dispersed through the reacting liquid by such means as physical agitation, gas-liquid sparger diffusion, gas-liquid flow eduction or other known gas-liquid contacting techniques.

A high pressure vent gas 15 is typically vented from the head of the reactor to prevent buildup of gaseous by-products such as methane, carbon dioxide and hydrogen and to maintain a set carbon monoxide partial pressure at a given total reactor pressure, and then flow to gas scrubbing system 2. A portion of the high pressure vent gas which contains carbon monoxide can also be used as a purge, via line 16, to the flasher base liquid to enhance rhodium stability.

Optionally (as illustrated in FIGS. 2 and 3), a so-called "converter" 1a can be employed which is located between the reactor 1 and flasher 3. The effluent from the reactor 1 is transferred to the converter through the reaction medium transfer line 14, and its effluent is transferred to flasher 3. Without the optional converter, the reactor 1 effluent would flow directly to the flasher 3. The "converter" 1a produces a vent stream comprising gaseous components, which are fed to the gas-scrubbing system 2 via line 15a and then scrubbed in the gas-scrubbing system 2, with a compatible solvent, to recover components such as methyl iodide and methyl acetate. The gaseous purge streams from the reactor and converter can be combined or scrubbed separately and are typically scrubbed with either acetic acid, methanol or mixtures of acetic acid and methanol to prevent loss of low boiling components such as methyl iodide from the process. As illustrated in FIG. 3, If methanol 10a is used as the vent scrub liquid solvent, the enriched methanol from the scrubbing system 2 is typically returned to the process via line 33 by combining it with the fresh methanol feeding the carbonylation reactor—although it can also be returned into any of the streams that recycle back to the reactor such as the flasher residue or light ends or drying column overhead streams. If acetic acid is used as the vent scrub liquid solvent, the enriched acetic acid from the scrubbing system is typically stripped of absorbed light ends and the resulting lean acetic acid is recycled back to the absorbing step. The light end components stripped from the enriched acetic acid scrubbing solvent can be returned to the main process directly or indirectly in several different locations including the reactor, flasher, or purification columns. Optionally, the gaseous purge streams may be vented through the flasher base liquid or lower part of the light ends column to enhance rhodium stability and/or they may be combined with other gaseous process vents (such as the purification column overhead receiver vents) prior to scrubbing. These variations are well known to those skilled in the art.

2. Flasher

Referring to FIG. 1, liquid product is drawn off from the carbonylation reactor 1 via line 14 at a rate sufficient to maintain a constant level therein and is introduced to the flasher 3 at an intermediate point between the top and bottom thereof. In the flasher 3 the catalyst solution is withdrawn as a base stream (catalyst recycle 13; predominantly acetic acid containing the rhodium and the iodide salt along with lesser quantities of methyl acetate, methyl iodide, and water), while the overhead of the flasher comprises largely crude acetic acid along with methyl iodide, methyl acetate, and water. This stream is fed to the light ends column 4 via line 17. A portion of the carbon monoxide along with gaseous by-products such as methane, hydrogen, and carbon dioxide exits the top of the flasher. The non-condensable gaseous components from the reactor vent line 15 and purification system vent line 31 that are not recovered, typically by scrubbing using acetic acid or methanol to capture and recover methyl iodide and other light boiling components from the vent streams, are purged from the plant via line 30. The recycled light ends 32 from the reactor vent can be returned to the process. The enriched acetic acid or methanol scrub liquid containing the light components recovered from streams 15 and 31 is returned to the process thereby preventing loss of the valuable light boiling components comprising methyl iodide and methyl acetate. The essential scrubbing of the vent gasses to recover methyl iodide and methyl acetate also has the effect of preventing the exit of formic acid from the process in these vents. As a consequence, there is no route for formic acid to be purged from the process other than to eventually exit as an impurity in the glacial acetic acid product.

3. Purification—Light Ends Column, Drying Column and Heavy Ends Column

Referring to FIGS. 1, 2, and 3, the crude acetic acid is typically drawn as a side stream near the base of the light ends column 4 via line 21 for further water removal in a drying column 6. The overhead distillate of the light ends column typically comprises water, methyl iodide, methyl acetate and some acetic acid. The light ends overhead stream 19 is commonly condensed and then separated through a light ends column decanter 5 into two phases consisting of a predominately aqueous phase 20 and a predominately organic phase 22. Both phases are directly or indirectly recycled back into the reaction medium. A residue stream can be taken from the light ends column which may contain some traces of rhodium catalyst entrained from the flasher vessel. The residue stream from the light ends column is typically returned to the flasher vessel or reaction medium via line 18, thereby returning the entrained rhodium and other entrained catalyst components.

The crude acetic acid from the light ends column 4 is further distilled in the drying column 6 to primarily remove the remaining water, methyl iodide and methyl acetate as an overhead distillate. The overhead vapor from the drying column is sent to a drying column reflux drum 7 via line 24. The net condensed overhead of the drying column is also recycled directly or indirectly back to the reaction medium via line 25. The residue 23 of the drying column 6 can be further treated if necessary to remove heavy ends (such as propionic acid) in a heavy ends column 8. The overhead product from the heavy ends column is transferred back to the drying column 6 via line 26. The heavy byproduct 27 of the heavy ends column 8 is purged. Alternatively, it can be treated directly by a "polishing" system to remove specific trace impurities such as iodides. The final glacial acetic acid product 28 can be the "polished" drying column residue or it can be a distillate or sidestream from the heavy ends column. Simple variations on the final purification are obvious to those skilled in the art and are outside the scope of the present invention.

By using a guard bed system to remove specific trace impurities such as iodides, the heavy ends column can be eliminated. Simple variations on the final purification are obvious to those skilled in the art and are outside the scope of the present invention.

Without a heavy ends treatment column or optional finishing distillation column, the removal of higher molecular weight iodides from the product stream is necessary in order to meet product specifications for iodide, especially for iodide-sensitive end uses such as the manufacture of vinyl acetate monomer, as will be appreciated by one of skill in the art.

C. Reaction Condition

1. Temperatures & Pressures

The temperature of the reactor is controlled automatically, and the carbon monoxide is introduced at a rate sufficient to maintain a constant total reactor pressure. The carbon monoxide partial pressure in the reactor is typically about 2 to 30 atmospheres absolute, preferably about 4 to 15 atmospheres absolute. Because of the partial pressure of by-products and the vapor pressure of the contained liquids, the total reactor pressure is from about 15 to 45 atmospheres absolute, with the reaction temperature being approximately 150° C. to 250° C. Preferably, the reactor temperature is about 175° C. to 220° C.

2. Reaction Rates

The rate of the carbonylation reaction according to the present state of the art has been highly dependent on water concentration in the reaction medium, as taught by U.S. Pat. No. 3,769,329; EP0055618; and Hjortkjaer and Jensen (1977). That is, as the water concentration is reduced below about 14-15 wt % water, the rate of reaction declines. The catalyst also becomes more susceptible to inactivation and precipitation when it is present in process streams of low carbon monoxide partial pressures. It has now been discovered, however, that increased acetic acid-production capacity can be achieved at water concentrations below about 14 wt % (at water contents above about 14 wt %, the reaction rate is not particularly dependent on water concentration) by utilizing a synergism which exists between methyl acetate and the iodide salt as exemplified by lithium iodide especially at low water concentrations.

D. Reaction Medium

1. Group VIII Metal Catalyst

The carbonylation between carbon monoxide and methanol is conducted in the presence of a Group VIII metal catalyst. Preferably, the Group VIII metal catalyst is rhodium and iridium. For example, the rhodium complex ($RhI_2(CO)_2$)—is used as a catalyst to prepare acetic acid. The concentration of rhodium catalyst used in the invention is about 200 ppm to about 2000 ppm.

2. Ranges of Components a) Methyl Iodide

Methyl iodide is a promoter of rhodium catalyst and its concentration is relevant to the reaction rate. The concentration of reactor methyl iodide used in the experiments mentioned in the invention was maintained between about 5 weight % and 20 weight % during the course of the experiments. If the concentration of methyl iodide is higher than 20 weight %, rhodium catalyst will be precipitated at an accelerated rate, which thus causes a loss of rhodium catalyst and increases the load of the downstream purification procedures as well as the productivity. However, a concentration of methyl iodide less than 5 weight % reduces much of the effectiveness to promote the rhodium catalyst and thus decreases the reaction rate. Therefore, the concentration of methyl iodide in the reactor of the invention should be maintained within the range between 5 weight % and 20 weight %.

b) Methyl Acetate

Methyl acetate will be formed in situ by the esterification of methanol and acetic acid. The concentration of methyl acetate is relevant to the reaction rate of methanol carbonylation and should be maintained in a proper range to provide an optimum reaction rate. High methyl acetate concentration causes precipitation and loss of rhodium catalyst. Further, if the concentration of methyl acetate is maintained below 0.5 weight %, the reaction rate will be too low to be economical. Therefore, the concentration of methyl acetate in the reactor is maintained in the range between 0.5 weight % and 30 weight %.

c) Water

According to the invention, the reactor water concentration ranges from 0.5 weight % to 14 weight %. Preferably, the reactor water concentration ranges from 0.5 weight % to 8 weight % and more preferably 0.5 weight % to 4 weight %.

3. Iodides

The iodide(s) used in the invention for conducting the carbonylation reaction to prepare acetic acid are iodide salts and methyl iodide. Maintaining iodide salts in the reaction medium is the most effective way to stabilize the rhodium catalyst in the methanol carbonylation reaction. The invention utilizes iodide salts to maintain iodide ions in an amount of 2 weight % to 20 weight % in the carbonylation reaction for preparing acetic acid. The iodide ions can be formed directly by adding soluble iodide salts or they can be formed in-situ by the addition or accumulation of various non-iodide salts such as metal acetates, hydroxides, carbonates, bicarbonates, methoxides and/or amines, phosphines, stilbines, arsenes, sulfides, sulfoxides or other compounds that are capable of generating iodide ions in the reaction medium through reaction with methyl iodide or HI. Non-limiting examples would include compounds such as lithium acetate, lithium hydroxide, lithium carbonate, potassium hydroxide, potassium iodide, potassium acetate, sodium hydroxide, sodium carbonate, sodium bicarbonate, sodium methoxide, calcium carbonate, magnesium carbonate, pyridine, imidazole, triphenyl phosphine, triphenyl phosphine oxide, dimethyl sulfide, dimethyl sulfoxide, polyvinyl pyridine, polyvinyl pyridine N-oxide, methylpyridinnium iodide and polyvinyl pyrrolidone.

E. Inhibition of the Formation of Formic Acid Impurities in Acetic Acid Product

1. Graph

Discovered that the formic acid formation is independent of other process parameters and appears to be directly correlated to the amount of water maintained in the reactor. As the water concentration in the reaction medium increases, the formic acid production and therefore concentration also increases. The concentration of formic acid in the glacial acetic acid product is an effective indicator of the water concentration in the reactor. The correlation of water to the formic acid in the final glacial acetic acid product can be expressed by applying mathematical curve fitting techniques to the experimental data. A multitude of curve fit equations can be easily derived and used to define the correlation between water and formic acid. According to one preferred embodiment of the invention, the correlation between water and formic acid is shown in FIG. 4.

2. Table

Variations in processes from one company to another and testing variations result in the inability for the formula described above to allow very precise control of the formic acid production in the methanol carbonylation process. Based on the correlation of formic acid to the water concentration maintained in the reaction medium, the following table was derived, which allows the selection of a specific range of formic acid based on ranges of water concentration.

| Target Formic Acid Concentration | Reactor Water Concentration |
| --- | --- |
| 15 to 35 ppm | 0.5 to 4 |
| 35 to 75 ppm | 4 to 8 |
| 75 to 100 ppm | 8 to 10 |
| 100 to 160 ppm | 10 to 14 |

However, one of ordinary skill in the art will understand that the ranges of formic acid described in the table will overlap those above and below the ranges recited at the transition point from one water concentration level to the next.

F. Control of Sulfer Impurity in Reaction Product of Rhodium-Catalyzed Methanol Carbonylation When a silver exchanged resin is used, it is typically a macroreticular (macroporous) strong acid cation exchange resin. According to the invention, the resin is stable up to about 100° C.; however, as the temperature increases, a gradual decrease in stability occurs so that the sulfonic groups of the resin can hydrolyzed to afford various soluble sulfur components which may leach into the acetic acid. Therefore, as the resin temperature increases from 25° C. to 100° C., the sulfur impurities may increase gradually, therefore the concentration of the sulfur impurities from the resin can be controlled carefully by adjusting the preferred operating temperature range for the resin to maximize iodide removal and minimize sulfur in the glacial acetic acid. A minimum temperature of 25° C. is sometimes employed while the minimum temperatures of about 50° C. and 70° C. may likewise be preferred in some embodiments. In general, when a silver exchanged strong acid cation exchange resin is employed typically from about 25% to about 75% of the active sites are converted to the silver form. Most typically about 50% of the active sites are so converted. At temperatures greater than about 50° C., the silver exchanged cation exchange resin may tend to release only small amounts of silver and sulfur on the order of 500 ppb or less and thus the silver or mercury exchanged substrate is chemically stable under the conditions of interest. More preferably silver losses are less than about 100 ppb into the organic medium and still more preferably less than about 20 ppb into the organic medium. Silver losses may be slightly higher upon start up or if the process is conducted such that it may be exposed to light, since silver iodide is photoreactive and may form soluble complexes if contacted by light. During the treatment, the sulfur will be leached from the resin and leaves in the glacial acetic acid product at an amount less than 1 ppm. Preferably, the sulfur leached from the resin and left in the glacial acetic acid product is in an amount ranging from 20 to 800 ppb. More preferably, the sulfur leached from the resin and left in the glacial acetic acid product is in an amount ranging from 20 to 600 ppb. More preferably, the sulfur leached from the resin and left in the glacial acetic acid product is in an amount ranging from 20 to 400 ppb. More preferably, the sulfur leached from the resin and left in the glacial acetic acid product is in an amount ranging from 20 to 200 ppb. More preferably, the sulfur leached from the resin and left in the glacial acetic acid product is in an amount ranging from 20 to 100 ppb. More preferably, the sulfur leached from the resin and left in the glacial acetic acid product is in an amount ranging from 20 to 50 ppb. Most preferably, the sulfur leached from the resin and left in the glacial acetic acid product is in an amount ranging from 20 to 40 ppb.

Suitably stable ion exchange resins utilized in connection with the present invention typically are of the "$RSO_3H$" type classified as "strong acid", that is, sulfonic acid, cation exchange resins of the macroreticular (macroporous) type. Particularly suitable ion exchange substrates include silver functionalized Amberlyst 15® resin from Rohm & Haas, being particularly suitable for use at elevated temperatures. Most typically the resin is a sulfonic acid functionalized resin, wherein from about 25 to about 75 percent of the active sites have been converted to the silver form, whereas the product stream, prior to contacting the resin, has an iodide content of greater than about 100 ppb organic iodide. After contacting the resin, the stream, which initially had greater than 100 ppb organic iodide, typically had less than 20 ppb iodide and more desirably has less than about 10 ppb organic iodide. Most preferably, the iodides can be were completely removed from the stream.

The process of the present invention may be carried out in any suitable configuration. A particularly preferred configuration is to utilize a bed of particulate material (termed herein a "guard bed") inasmuch as this configuration is particularly convenient. A typical flow rate, such as is used when acetic acid is to be purified, is from about 0.5 to about 20 bed volumes per hour (BV/hr). A bed volume of organic medium is simply a volume of the medium equal to the volume occupied by the resin bed. A flow rate of 1 BV/hr then means that a quantity of organic liquid equal to the volume occupied by the resin bed passes through the resin bed in a one hour time period. Preferred flow rates are usually from about 6 to about 10 BV/hr whereas a preferred flow rate is frequently about 6 BV/hr.

According to one embodiment of the invention, the apparatus of the invention includes a reactor, a flasher, a light ends column, a drying column, a heavy ends column and a resin bed. Crude acetic acid product is manufactured by rhodium-catalyzed methanol carbonylation as previously described. The acetic acid product is fed to the resin bed used for controlling trace iodide impurities in the reaction product of rhodium-catalyzed methanol carbonylation. The resin bed is a bed of silver exchanged cation exchange media and is typically operated at an average product temperature of greater than about 50° C.

The present invention is better understood by reference to the following examples. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the invention.

VI. EXAMPLES

A. Testing of Correlation Between Reactor Water Concentration and Formic Acid in Product Glacial Acetic Acid The following experimental runs were carried out in a continuously operating system comprising the equipment and components previously described hereinabove. The liquid reaction medium in the reactor was maintained between 7 and 13 weight % methyl iodide, 1 to 3.2 weight % methyl acetate, 0.4 to 11.5 weight % iodide ion, 1.7 to 14.6 weight % water, and 500 to 1300 ppm of rhodium. The balance of the reaction medium was essentially acetic acid.

During experiments, the reactor temperature was maintained between about 189 to 199° C. The pressure was maintained at about 26 to 28 atmospheres absolute. Carbon monoxide was continuously introduced through a sparger situated below the mechanical agitator blades, and a continuous vent of gas was drawn off from the top of the vapor space contained in the upper part of the reactor. The reactor vent and other non-condensable gasses collected from the purification train were scrubbed with acetic acid to prevent losses of methyl iodide and other low boiling components contained in the vent streams. The light end components from the acetic acid scrubbing system were continuously returned to the process and the low boiling components (including formic acid) in the vent streams were thus retained in the process. The carbon monoxide partial pressure in the reactor headspace was maintained at about 4 to 9 atmospheres absolute.

By means of a level control sensing the liquid level within the reactor, liquid reaction product was continuously drawn off and fed into a flasher vessel operating at a head pressure of about 3 atmospheres absolute. The vaporized portion of the introduced catalyst liquid exiting the overhead of the flasher was distilled in the light ends column.

The light ends column was used to separate and recycle primarily methyl iodide, methyl acetate and a portion of the water from the crude acetic. A sidestream from the light ends column was drawn off as the crude acetic acid to feed a drying column for further purification.

A drying column was then used to remove the remaining water, methyl iodide and methyl acetate from the crude acetic acid. The distillate of the drying column was combined with the distillate from the light ends column and recycled back to the reaction section. The residue of the drying column was fed to a heavy ends column where the heavy ends (primarily propionic acid) was removed in the residue and the distilled product glacial acetic acid was measured for formic acid content.

The contents of formic acid in the final glacial acetic acid product were analyzed by GC/TCD method periodically throughout the experiments. It was found that the reactor water concentration was directly proportional to the formic acid in the purified glacial acetic acid product. The relationship can be clearly seen as a function of the water concentration in the reaction medium within reactor water concentrations of 1.7 to 14.6 weight % (See the table below and FIG. 4). One predictive curve fit equation defining the relationship between reactor water and product formic acid is also illustrated in FIG. 4.

TABLE 1

Correlation of Formic Acid in Glacial Acetic Acid Product to Water Concentration in the Carbonylation Reaction Medium

| Glacial Acetic Acid Product Formic Acid Impurity (ppm) | Reaction Medium Water Concentration (weight %) |
|---|---|
| 18 | 2.02 |
| 21 | 1.73 |
| 22 | 1.83 |
| 22 | 1.81 |
| 23 | 1.96 |
| 24 | 1.92 |
| 24 | 1.81 |
| 24 | 1.7 |
| 25 | 1.85 |
| 28 | 4.8 |
| 30 | 4.9 |
| 30 | 5 |
| 32 | 5.5 |
| 40 | 5.6 |
| 42 | 3.8 |
| 47 | 4.4 |
| 52 | 5.4 |
| 53 | 5.2 |
| 62 | 4.2 |
| 73 | 8.7 |
| 86 | 11.3 |
| 90 | 11 |
| 96 | 10 |
| 97 | 11.5 |
| 108 | 10.5 |
| 111 | 12 |
| 116 | 10.8 |
| 118 | 11 |
| 124 | 11.2 |
| 126 | 11.2 |
| 126 | 10.6 |
| 128 | 11.5 |
| 132 | 12.1 |
| 132 | 11.9 |
| 139 | 11.5 |
| 156 | 14.6 |
| 157 | 14.3 |
| 166 | 14 |
| 166 | 13.6 |
| 173 | 14.5 |
| 176 | 14.3 |
| 216 | 14.4 |

B. Detection of Sulfur Left in Product Glacial Acetic Acid

Samples of acetic acid (drying column residue) from a rhodium-catalyzed methanol carbonylation process as mentioned hereinbefore was treated using a silver functionalized strong acid macroreticular (macroporous) cation exchange resin (such as Amberlyst 15® from Rohm & Haas) guard bed at 25° C., 50° C. and 75° C. Results appear in the following Table 2. As can be seen from Table 2, the sulfur shows a steady loss of about 200 ppb at the above three temperatures.

| Runs | Sulfur, ppb |
|---|---|
| 25° C. (77° F.) | 200 |
| 50° C. (122° F.) | 200 |
| 75° C. (167° F.) | 200 |

While the present invention has been described in detail and exemplified, various modifications will be readily apparent to those of skill in the art. For example, one may utilize an ion exchange resin suited for higher temperatures in connection with the present invention. Such modifications are within the spirit and scope of the present invention, which is defined in the appended claims.

What is claimed is:

1. A method of controlling impurities in a rhodium-catalyzed methanol carbonylation process for the manufacture of a glacial acetic acid product, comprising:
    a) reacting methanol, methyl acetate, dimethyl ether or mixtures thereof with carbon monoxide in the presence of a rhodium catalyst in a reaction vessel;
    b) maintaining in said reaction vessel a water concentration of 0.5 to 14 weight percent; such that the formic acid content in the resulting final glacial acetic acid product is controlled to an amount ranging from 15 ppm to 160 ppm; and
    c) contacting the acetic acid obtained from step b) with a silver exchanged cation exchange resin so that the total sulfur in the resulting final glacial acetic acid is in an amount less than 1 ppm,
    wherein the concentration of the formic acid in the final glacial acetic acid product is controlled by controlling the reaction vessel water concentration according to a mathematical correlation between the reactor water concentration and the formic acid concentration, the mathematical correlation being empirically determined by curve fitting data obtained by varying the reactor water concentration in the reaction vessel and measuring the formic acid concentration in the final glacial acetic acid product produced at a particular reactor water concentration.

2. The method of claim 1, wherein the silver exchanged cationic ion exchange resin is a silver functionalized strong acid macroreticular cation exchange resin.

3. The method of claim 1, which maintains a reactor water concentration of 0.5 to 10 weight percent for the manufacture of acetic acid so that the glacial acetic acid product contains a formic acid content of 15 ppm to 100 ppm.

4. The method of claim 1 which maintains a reactor water concentration of 0.5 to 8 weight percent for the manufacture of acetic acid so that the glacial acetic acid product contains a formic acid content of 15 ppm to 75 ppm.

5. The method of claim 1 which maintains a reactor water concentration of 0.5 to 4 weight percent for the manufacture of acetic acid so that the glacial acetic acid product contains a formic acid content of 15 ppm to 35 ppm.

6. The method of claim 1 wherein the glacial acetic acid product contains the total sulfur content of from 20 ppb to 800 ppb.

7. The method of claim 1 wherein the glacial acetic acid product contains the total sulfur content of from 20 ppb to 600 ppb.

8. The method of claim 1 wherein the glacial acetic acid product contains the total sulfur content of from 20 ppb to 400 ppb.

9. The method of claim 1 wherein the glacial acetic acid product contains the total sulfur content of from 20 ppb to 200 ppb.

10. The method of claim 1 wherein the glacial acetic acid product contains the total sulfur content of from 20 ppb to 100 ppb.

11. The method of claim 1 wherein the glacial acetic acid product contains the total sulfur content of from 20 ppb to 50 ppb.

12. The method of claim 1 wherein the glacial acetic acid product contains the total sulfur content of from 20 ppb to 40 ppb.

13. The method of claim 1 wherein the mathematical correlation between the reactor water concentration and the formic acid concentration is:

$Y = 5.7327 * \ln(X) - 15.923$, wherein Y= Reactor water concentration in wt % and X = formic acid concentration in the final glacial acetic acid product in parts per million.

14. The method of claim 1 wherein the mathematical correlation between the reactor water concentration and the formic acid concentration is:

$Y = -0.0003 * X^2 + 0.1417 * X - 0.6262$, wherein Y= Reactor water concentration in wt % and X= formic acid concentration in the final glacial acetic acid product in parts per million.

* * * * *